United States Patent [19]
Roberts

[11] Patent Number: 6,124,520
[45] Date of Patent: *Sep. 26, 2000

[54] WINDOW DRESSING

[75] Inventor: Jerry H. Roberts, Okemos, Mich.

[73] Assignee: Tri-State Hospital Supply Corporation, Howell, Mich.

[ * ] Notice: This patent issued on a continued prosecution application filed under 37 CFR 1.53(d), and is subject to the twenty year patent term provisions of 35 U.S.C. 154(a)(2).

[21] Appl. No.: 08/918,211

[22] Filed: Aug. 25, 1997

[51] Int. Cl.$^7$ ...................................................... A61F 13/00
[52] U.S. Cl. ............................... 602/54; 602/42; 602/52; 602/56; 602/57
[58] Field of Search ............................... 604/180; 602/57, 602/58, 59, 41; 128/888, 889; 206/440, 441

[56] References Cited

U.S. PATENT DOCUMENTS 5,713,842  2/1998  Kay ........................................... 602/57

*Primary Examiner*—Kim M. Lee
*Attorney, Agent, or Firm*—Fildes & Outland, P.C.

[57] ABSTRACT

A self adherent window dressing includes a fabric tape layer having an adhesive side and an opposite non-adhesive side. The fabric tape layer has an opening therein to allow viewing of a wound or injection site therethrough. A semi-permeable transparent film layer closes the opening in the fabric tape layer. The transparent film layer has an adhesive side and an opposite non-adhesive side. The film layer adhesive side is adhered on the non-adhesive side of the fabric layer around the opening. An absorbent fiber layer having an opening generally corresponding to the opening in the fabric tape layer is mounted on the adhesive side of the fabric tape layer such that the openings in the absorbent fiber and fabric tape layers are in alignment and the fabric tape layer extends beyond the periphery of the absorbent fiber layer. A non-adherent porous film layer of a shape generally corresponding to the shape of the absorbent layer is adhered to the fiber layer.

11 Claims, 1 Drawing Sheet

WINDOW DRESSING

FIELD OF THE INVENTION

This invention relates to transparent dressings for the protection of wounds or indwelling catheters and more particularly to a self adherent window dressing that provides for continual visual access to the wound or indwelling catheter together with a fluid absorption system.

BACKGROUND OF THE INVENTION

It is known in the art relating to dressings for the protection of wounds or indwelling catheters to use self-adherent protective bandage tape or clear film product alternatives that use non-sensitizing hypoallergenic adhesives to cover all or part of the intravenous catheter site. Some dressings combine non-woven tape and absorbent gauze-like materials which have surfaces of non-adherent film to reduce the effect of adhesive stripping. The absorbency and bacterial barrier of the pad typically varies minimally from one manufacturer to another, but this type of dressing is least occlusive to moisture vapor.

Conventional transparent type dressings are associated with greater accumulations of moisture, blood or serum underneath their protective film layers and consequently experience higher rates of insertion site colonization. The need exists for a transparent type dressing having the ability to absorb fluids from the wound it covers or the surface of the skin on which it is mounted.

SUMMARY OF THE INVENTION

The present invention provides a self adherent window dressing or bandage having an absorbent pad dressing generally surrounding a semipermeable transparent cover permitting visual inspection of a wound or insertion site and circumfluent absorption of fluid around the wound or site.

More specifically, the present invention is a self adherent window dressing including a fabric tape layer having an adhesive side and an opposite non-adhesive side. The fabric tape layer has an opening therein to allow viewing of a wound or injection site therethrough. A semipermeable transparent film layer closes the opening in the fabric tape layer. The transparent film layer has an adhesive side and an opposite non-adhesive side. The film layer adhesive side is adhered on the non-adhesive side of the fabric layer around the opening.

An absorbent fiber layer having an opening generally corresponding to the opening in the fabric tape layer is mounted on the adhesive side of the fabric tape layer such that the openings in the absorbent fiber and fabric tape layers are in alignment and the fabric tape layer extends beyond the periphery of the absorbent fiber layer. A non-adherent porous film layer of a shape generally corresponding to the shape of the absorbent fiber layer is defined by a laminated film which allows permeation from the surface of the wound or skin without causing either layer, non-adherent porous film and absorbent fiber, to "stick" when removed.

The window dressing also includes a removable silicone, or other non-stick, coated paper of a shape corresponding to the shape of said fabric tape layer. This paper is disposed over the absorbent fiber and non-adherent porous film layers against the adhesive side of the fabric tape layer extending beyond the absorbent fiber layer periphery. The non-stick paper also covers the semipermeable transparent film layer.

Preferably, the semipermeable transparent film layer comprises a liquid impermeable polyurethane film coated with a medical grade adhesive. This polyurethane film is gas permeable and impermeable to bacterial, viral, or other microcontaminants.

The fabric layer adhesive side may be coated with a hypoallergenic adhesive that is non-sensitizing.

Preferably, the non-adherent porous film layer comprises polyethylene film that wicks moisture inwardly.

In a preferred embodiment, the absorbent layer is a lint free, nonwoven fabric.

These and other features and advantages of the invention will be more fully understood from the following detailed description of the invention taken together with the accompanying drawings.

DETAILED DESCRIPTION OF THE INVENTION

Figure 1:
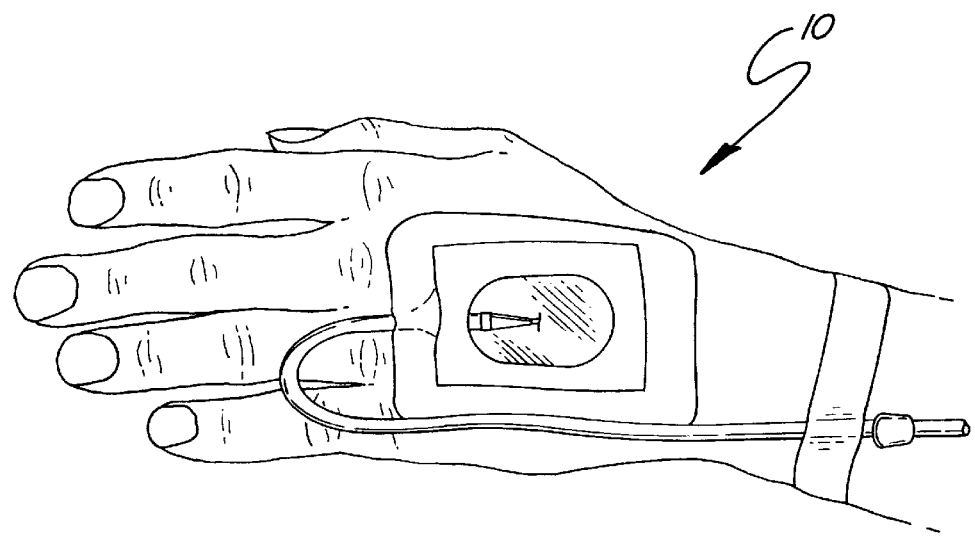
FIG. 1 is an environmental view of a self adherent window dressing constructed in accordance with the present invention adhered about an injection site in the hand of a patient.

Referring now to the drawings in detail, numeral 10 generally indicates a self adherent window dressing used on a patient for the protection of a wound or indwelling catheter. As is hereinafter more fully described, the window dressing 10 permits continuous visual inspection of the site and combines a lint-free, highly-absorbent pad that reduces moisture accumulation that heretofore has obscured the site. Furthermore, the dressing 10 possesses high oxygen and moisture permeability, and provides an impermeable barrier to liquids and bacteria.

Figure 2:
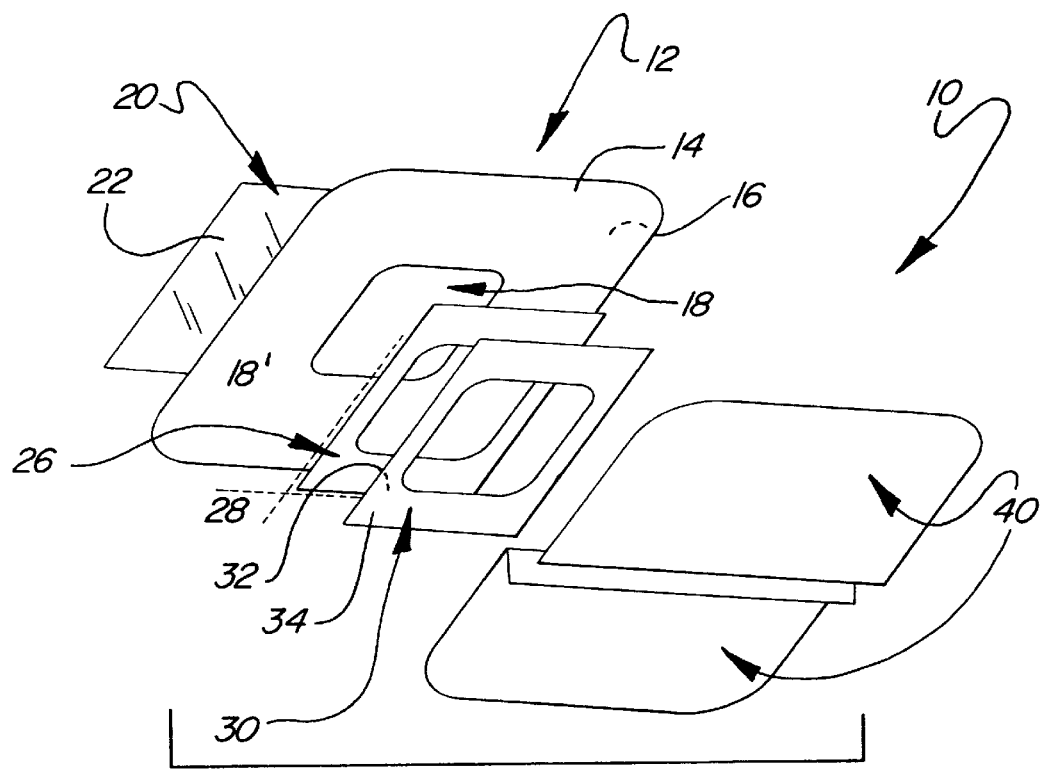
FIG. 2 is an exploded view of the self adherent window dressing of the invention illustrating its layered construction.

As illustrated in FIG. 2, the window dressing 10 includes a breathable, nonwoven fabric tape layer 12 having an adhesive side 14 and an opposite non-adhesive side 16. Preferably, the fabric layer adhesive side 14 is coated with a hypoallergenic adhesive that is non-sensitizing. The fabric tape layer 12 has an opening 18 therein to allow viewing of a wound or injection site, as illustrated in FIG. 1. A semipermeable transparent film layer 20 closes the opening 18 in the fabric tape layer 12. Preferably, the semipermeable transparent film layer 20 comprises a liquid impermeable, bacterial static polyurethane film. Preferably, the polyurethane film 20 is also gas and moisture vapor permeable, providing a high level of moisture vapor and gas (oxygen) exchange, for maintaining normal function of the skin on which it is mounted.

The transparent film layer 20 has an adhesive side 22 coated with a medical grade adhesive and an opposite non-adhesive side. The film layer adhesive side 22 is adhered on the non-adhesive side 16 of the fabric layer 12 around the opening 18 and adheres on the surface of the skin as illustrated in FIG. 1.

An absorbent fiber layer 26 having an opening 18', generally corresponding to the opening 18 in the fabric tape layer 12, is mounted on the adhesive side 14 of the fabric tape layer such that the openings 18,18' in the absorbent fiber and fabric tape layers are in alignment and the fabric tape layer extends beyond the periphery 28 of the absorbent fiber layer. Absorbent fiber layer 26 provides circumfluent moisture absorption around the opening 18 keeping the viewing area clear and dry. Absorbent fiber layer 26 also provides a cushion for a catheter when the dressing 10 is used over an injection site. Preferably, the absorbent fiber layer 26 is a nonwoven fabric. Absorbent fiber layer 26 may include an opening or slot therein for directing a tube extending from an insertion catheter or the like covered by the dressing 10.

A non-adherent porous film layer 30 of a shape generally corresponding to the shape of the absorbent layer 26 is defined by a laminated film which allows permeation from the surface of the wound or skin without causing either layer, non-adherent porous film and absorbent fiber, to "stick" when removed. In the illustrated embodiment, non-adherent porous film layer is adhered to the absorbent fiber layer by heat lamination. The non-adherent porous film layer 30 can be a polyethylene film or other suitable material that will not stick to the site or aggravate the wound upon removal.

The window dressing 10 also includes a removable silicone-coated, or other non-stick paper 40 of a shape corresponding to the shape of said fabric tape layer 12. This paper 40 is disposed over the absorbent 26 and non-adherent porous film 30 layers against the adhesive side 14 of the fabric tape layer extending beyond the absorbent fiber layer periphery. Paper 40 may be of one piece or multiple piece construction and is removed to allow the adhesive side 14 of the fabric tape layer 12 to be adhered to a patient.

Although the invention has been described by reference to a specific embodiment, it should be understood that numerous changes may be made within the spirit and scope of the inventive concepts described. Accordingly, it is intended that the invention not be limited to the described embodiment, but that it have the full scope defined by the language of the following claims.

What is claimed is:

1. A self adherent window dressing comprising:
   a fabric tape layer having an adhesive side and an opposite non-adhesive side; said fabric tape layer having an opening therein to allow viewing therethrough;
   a skin adhering, gas permeable, liquid impermeable transparent film layer closing said opening in said fabric tape layer and having an adhesive side and an opposite non-adhesive side; said film layer adhesive side being adhered on the non-adhesive side of said fabric tape layer around said opening and on the surface of the skin on which it is mounted for maintaining normal skin function;
   a wicking fiber layer having an opening generally corresponding to said opening in said fabric tape layer, said fiber layer mounted on the adhesive side of said fabric tape layer such that said openings in said wicking fiber and fabric tape layers are in alignment and said fabric tape layer extends beyond the periphery of said wicking fiber layer; and
   a non-adherent porous film layer of a shape generally corresponding to the shape of said wicking fiber layer adhered to said wicking fiber layer.

2. The window dressing of claim 1 including a removable paper of a shape corresponding to the shape of said fabric tape layer, said paper disposed over said absorbent and non-adherent porous film layer against the adhesive side of said fabric tape layer extending beyond said absorbent fiber layer periphery.

3. The window dressing of claim 2 wherein said paper is silicone-coated.

4. The window dressing of claim 1 wherein said gas permeable, liquid impermeable transparent film layer comprises a liquid impermeable polyurethane film coated with a medical grade adhesive.

5. The window dressing of claim 4 wherein said polyurethane film is impermeable to microcontaminants.

6. The window dressing of claim 1 wherein said fabric layer adhesive side is coated with a hypoallergenic adhesive.

7. The window dressing of claim 1 wherein said wicking fiber layer is a lint free, nonwoven fabric.

8. The window dressing of claim 1 wherein said wicking fiber layer includes an opening therein.

9. The window dressing of claim 1 wherein said non-adherent porous film layer comprises polyethylene film.

10. The window dressing of claim 9 wherein said polyethylene film is heat laminated to said absorbent fiber layer.

11. A self adherent window dressing comprising:
    a fabric tape layer having an adhesive side coated with a hypoallergenic adhesive and an opposite non-adhesive side; said fabric tape layer having an opening therein to allow viewing therethrough;
    a gas and moisture vapor permeable, liquid impermeable transparent film layer closing said opening in said fabric tape layer and having an adhesive side and an opposite non-adhesive side; said film layer adhesive side being adhered on the non-adhesive side of said fabric layer around said opening;
    a wicking, nonwoven fiber layer having an opening generally corresponding to said opening in said fabric tape layer, said fiber layer mounted on the adhesive side of said fabric tape layer such that said openings in said fiber and fabric tape layers are in alignment and said fabric tape layer extends beyond the periphery of said wicking fiber layer; and
    a non-adherent porous film layer of a shape generally corresponding to the shape of said wicking fiber layer adhered to said fiber layer.

* * * * *